United States Patent
Huang et al.

(10) Patent No.: US 9,554,869 B1
(45) Date of Patent: Jan. 31, 2017

(54) BITE TRAY HAVING FIDUCIAL MARKERS FOR HEAD SCAN REGISTRATION AND METHOD OF USE

(71) Applicants: Jerry T. Huang, City of Industry, CA (US); Ta-Ko Huang, Kaohsiung (TW)

(72) Inventors: Jerry T. Huang, City of Industry, CA (US); Ta-Ko Huang, Kaohsiung (TW)

(73) Assignee: EPED Inc., Kaohsiung (TW)

( * ) Notice: Subject to any disclaimer, the term of this patent is extended or adjusted under 35 U.S.C. 154(b) by 0 days.

(21) Appl. No.: 15/146,366

(22) Filed: May 4, 2016

Related U.S. Application Data

(60) Provisional application No. 62/276,434, filed on Jan. 8, 2016.

(51) Int. Cl.
*A61C 1/00* (2006.01)
*A61C 3/00* (2006.01)
(Continued)

(52) U.S. Cl.
CPC .............. *A61B 90/39* (2016.02); *A61B 5/055* (2013.01); *A61B 6/14* (2013.01); *A61B 90/13* (2016.02);
(Continued)

(58) Field of Classification Search
CPC .................... A61C 9/0006; A61B 2090/3937; A61B 2090/3762; A61B 2090/3995; A61B 2090/3983; A61B 2090/3912; A61B 2090/374; A61B 2090/3966; A61B 2090/3954
(Continued)

(56) References Cited

U.S. PATENT DOCUMENTS

| 4,618,978 A | 10/1986 | Cosman |
| 5,769,861 A | 6/1998 | Vilsmeier |

(Continued)

FOREIGN PATENT DOCUMENTS

| DE | 19619761 A1 | 11/1996 |
| GB | 2213066 A | 8/1989 |

OTHER PUBLICATIONS

R.Ewers et al., Basic research and 12 years of clinical experience in computer assisted navigation technology, Int. J. Oral Maxillofac Surg., 2005; 1-8; 34, Elsevier Ltd., AUT.

*Primary Examiner* — Matthew Nelson
(74) *Attorney, Agent, or Firm* — Timothy Thut Tyson; Law Office of Lawrence S. Cohen

(57) ABSTRACT

The present invention is directed to a bite tray having fiducial markers for head scan registration and method of use. The bite tray is held by a patient in his teeth while the scan of his head and the fiducial markers is made by x-ray, CT, or MM and the scan is entered into a computer to register the scan to the fiducial markers. Instrument optical markers are placed on a dental instrument and it is observed by a camera and the observation is entered into the computer to register the instrument optical markers to the dental instrument. Patient optical markers are placed on the patient and it is observed by the camera and the observation is entered into the computer to register the patient optical markers to the patient. The tip of the dental instrument is then touched to one of the fiducial markers making the location of the tip and the fiducial marker the same. The computer then registers the scan to the instrument and the patient. The bite tray is then removed from the mouth allowing access by the dentist to the teeth. The camera follows the movement of the instrument optical markers to (Continued)

the patient optical markers to create a display of the instrument and tip on the scan.

5 Claims, 12 Drawing Sheets

(51) Int. Cl.
*A61C 9/00* (2006.01)
*A61C 3/02* (2006.01)
*A61C 1/08* (2006.01)
*A61B 5/055* (2006.01)
*A61B 6/14* (2006.01)

(52) U.S. Cl.
CPC .............. *A61C 1/082* (2013.01); *A61C 3/02* (2013.01); *A61C 9/0006* (2013.01); *A61B 2090/374* (2016.02); *A61B 2090/3762* (2016.02); *A61B 2090/3912* (2016.02); *A61B 2090/3937* (2016.02); *A61B 2090/3954* (2016.02); *A61B 2090/3966* (2016.02); *A61B 2090/3983* (2016.02); *A61B 2090/3995* (2016.02)

(58) Field of Classification Search
USPC ..... 433/29, 37, 44, 68, 72, 73, 75, 214, 215
See application file for complete search history.

(56) References Cited

U.S. PATENT DOCUMENTS

| | | | |
|---|---|---|---|
| 5,947,981 A | 9/1999 | Cosman | |
| 6,223,067 B1* | 4/2001 | Vilsmeier | A61B 90/16 378/170 |
| 6,978,167 B2* | 12/2005 | Dekel | G06K 9/3216 356/620 |
| 8,226,651 B2 | 7/2012 | Gill et al. | |
| 8,238,631 B2 | 8/2012 | Hartmann et al. | |
| 9,084,535 B2 | 7/2015 | Girkin et al. | |
| 2002/0095081 A1* | 7/2002 | Vilsmeier | A61B 6/12 600/407 |
| 2006/0240378 A1* | 10/2006 | Weinstein | A61B 5/103 433/76 |
| 2010/0305580 A1* | 12/2010 | Henderson | A61B 19/52 606/130 |
| 2011/0052008 A1* | 3/2011 | Holsing | G06T 7/0018 382/103 |
| 2011/0217667 A1* | 9/2011 | Groscurth | A61C 9/004 433/68 |
| 2013/0322719 A1* | 12/2013 | Dekel | A61B 6/12 382/131 |
| 2015/0289960 A1* | 10/2015 | Shigemoto | A61B 5/1077 433/27 |

* cited by examiner

BITE TRAY HAVING FIDUCIAL MARKERS FOR HEAD SCAN REGISTRATION AND METHOD OF USE

TECHNICAL FIELD

The present invention pertains generally to head scanning procedures, and more particularly to a bite tray having fiducial markers for registration of head scans and method of use for guiding an instrument during head surgery.

BACKGROUND OF THE INVENTION

Surgical navigation systems using computers and monitors that register the locations of surgical instrument in relation to the patient are known in the art. An article titled "Basic research and 12 years of clinical experience in computer-assisted navigation technology: a review" by R. Ewers, et al. shows a setup for operating on a dental patient using an infrared camera to monitor tracking sensors attached to a surgical instrument and the head of the patient. Fiducial markers are placed on the patient before the CT scan is made. The tracking system picks up the positions of the patient and the surgical instrument and transfers them to a computer for registration.

FIG. 1 shows a prior art template 200 for use in dental implant surgery. Reference ceramic balls 202 are positioned over the desired positions for the implants. The balls are held in position for the scan by the vacuum formed template. FIG. 2 shows another prior art vacuum formed template 204 with pins 206 representing the proposed implant locations held in place at the desired locations. The x-ray or CT scan is then made and the results are used for planning purposes with respect to bone availability and mucosal thickness. The exact implant positions, diameters, and lengths can be determined. The templates are then removed for any actual oral surgery. No real time review and planning is possible using these fixtures.

A system for registering scans of the head and display of instruments on the scans in real time would be an advantage to oral and other surgeons.

BRIEF SUMMARY OF THE INVENTION

The present invention is directed to a bite tray having fiducial markers for registering scans of the head of a patient and method of use. The bite tray is positioned between the teeth of a patient. An inside teeth perimeter ridge is inside of the teeth and an outside teeth perimeter ridge is outside the teeth. Fiducial markers are positioned in fiducial marker holders outside of the outside teeth ridge. A settable compound is put in the bite tray. The patient bites into the settable compound making impressions of the teeth. The bite tray is then removed allowing the settable compound to set. The bite tray with the permanent impressions is then reinserted between the teeth and a x-ray, CT, or MM scan is made of the head of the patient. The fiducial markers appear on the scan allowing the orientation of the scan to be registered on a data processing device and displayed. The instrument that is to be used for a procedure has an operating tip and instrument optical or magnetic markers. It is detected by a spatial tracking device such as an optical camera, infrared camera, or magnetic sensor and the data is sent to the data processing device to register the relationship of the operating tip to the markers on the instrument. Patient optical or magnetic markers are mounted on the patient's head away from the jaw. When the operating tip of the instrument is touched to a fiducial marker in the bite tray, the spatial tracker observes the instrument markers and patient markers and transmits the data to the data processing device. The data processing devices uses the data to compute and register the relationships of the instrument and patient optical or magnetic markers to the scan image of the patient's head and displays the computed image of the instrument superimposed on the scan image. The bite tray is then removed from the patient. When the head or oral surgeon moves the instrument, the spatial tracker observes the instrument markers and the patient markers and transmits the data to the data processing device. The data processing device computes the relationship between the current position of the operating tip based on the current positions of the instrument and patient optical or magnetic markers and displays the computed image of the operating tip and instrument in the new position superimposed on the scan image of the head for monitoring by the head or oral surgeon.

In an embodiment, the patient markers are attached to the top of the head of the patient and the bite tray is removed for work on the upper jaw. The patient can then open his jaw and the operating tip of the instrument is moved by the oral surgeon for work on the upper jaw. The positions of the instrument markers and patient markers are continuously observed by the spatial tracker and delivered to the data processing device. The data processing device uses the data to present an image of the instrument with the operating end superimposed on the scan of the head of the patient.

In another embodiment, the patient markers are attached to the lower jaw of the patient for procedures on the lower jaw. After the impressions are made in the bite tray, the bite tray is left on the lower jaw and the lower jaw is lowered for the x-ray, CT, or MRI scan. The bite tray is then removed for work on the lower jaw.

In yet another embodiment, the patient markers are attached to the side of the head of the patient for procedures on the head. After the x-ray, CT, or MM scan is made of the head with the bite tray in place, the bite tray is removed for procedures on the head. The patient can then open his jaw for insertion of instruments into the mouth or anesthesia apparatus over the nose and mouth.

Other embodiments, in addition to the embodiments enumerated above, will become apparent from the following detailed description, taken in conjunction with the accompanying drawings that illustrate, by way of example, the principles of the bite registration device and method of use.

DETAILED DESCRIPTION OF THE INVENTION

Figure 1:
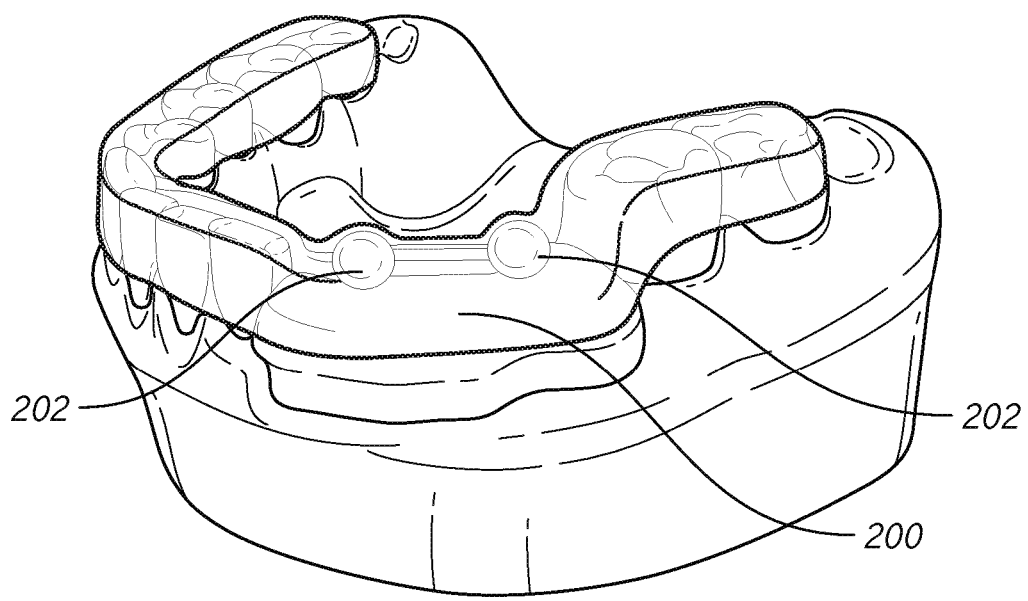
FIG. 1 is a perspective view of a prior art template for holding reference ceramic balls in place for a scan of the jaw.
Figure 2:
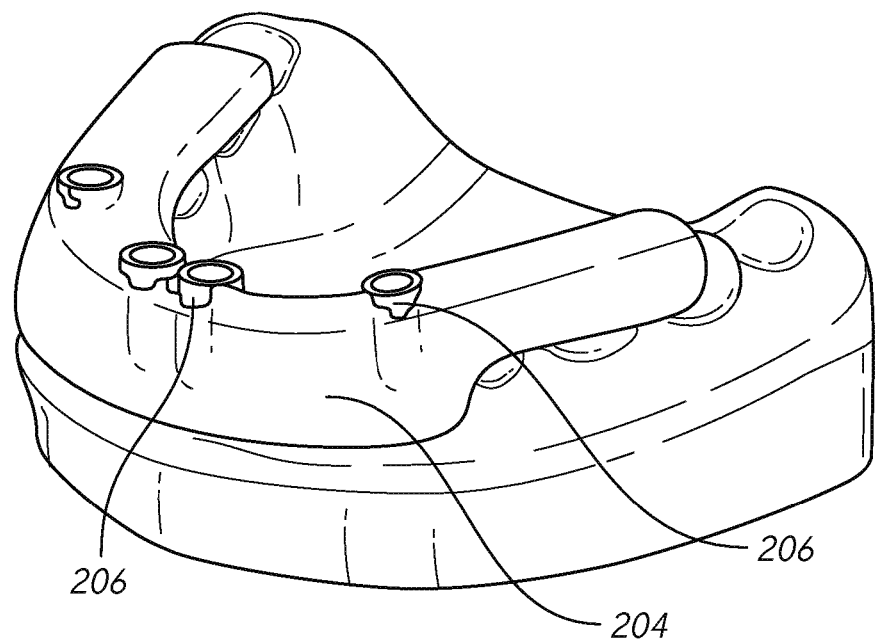
FIG. 2 is a perspective view of a prior art template for holding reference pins in place for a scan of the jaw.
Figure 3:
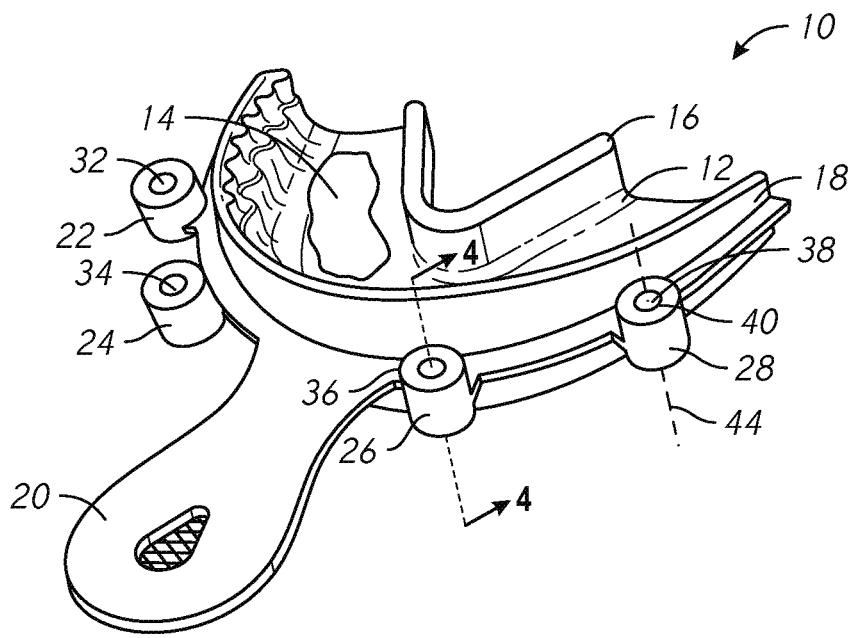
FIG. 3 illustrates a bite tray having fiducial markers in fiducial marker holders outside the outer teeth perimeter and a settable compound inside.
Figure 4:
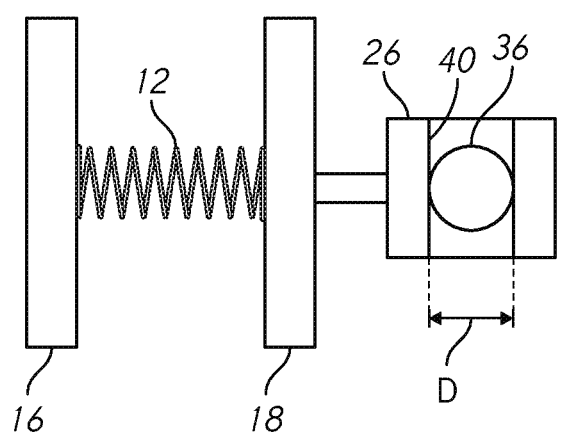
FIG. 4 is a sectional view through one of the fiducial marker holders.

Referring initially to FIG. 3, a bite tray in accordance with the present invention is shown generally designated as 10 for use in making x-ray, CT, or MRI scans of the head. A substantially planar floor 12 is positionable between the upper and lower teeth of a patient when they are clamped together. The floor is typically a nylon mesh for retaining a settable compound 14 such as alginate or vinyl polysiloxane that is added on both sides before the tray is inserted into the patient's mouth. An inside teeth perimeter ridge 16 is coupled to the floor for fitting inside the upper and lower teeth of the patient. An outside teeth perimeter ridge 18 is coupled to the floor for fitting outside of the teeth of the patient. A handle 20 facilitates the placement of the bite tray into and out of the mouth of the patient. Fiducial marker holders 22, 24, 26, and 28 are positioned outside of the outside teeth perimeter ridge. Fiducial markers 32, 34, 36, and 38 are located inside. Each holder has a substantially cylindrical aperture 40 with a longitudinal axis 44 substantially perpendicular to the planar floor 12. FIG. 4 is a sectional view along line 4-4 of FIG. 3 showing fiducial marker 36 in the form of a ceramic ball positioned inside the substantially cylindrical aperture 40. Ceramic balls are selected for the fiducial markers because they have a density substantially the same as bone and therefore show on a scan of the bone structure of the head. The preferred diameter D of the aperature is substantially the diameter of a drill bit shank. When a drill bit shank is inserted into an aperature to abut a ceramic ball, it is perpendicular to the plane of the floor of the bit tray and the closed teeth and is used for registering the operating tip to the scan of the head.

Alternatively, any material having a density substantially the same as bone may be used to create the fiducial markers. And they do not have to be spherical so long as the center of the shape can be determined. They may also be affixed to the bite tray by being inlayed or glued to the bite tray instead of in holders. An upper or lower bite tray may also be used instead of a whole tray. The settable compound 14 is then used only on the side that concerns the procedure.

Figure 5:
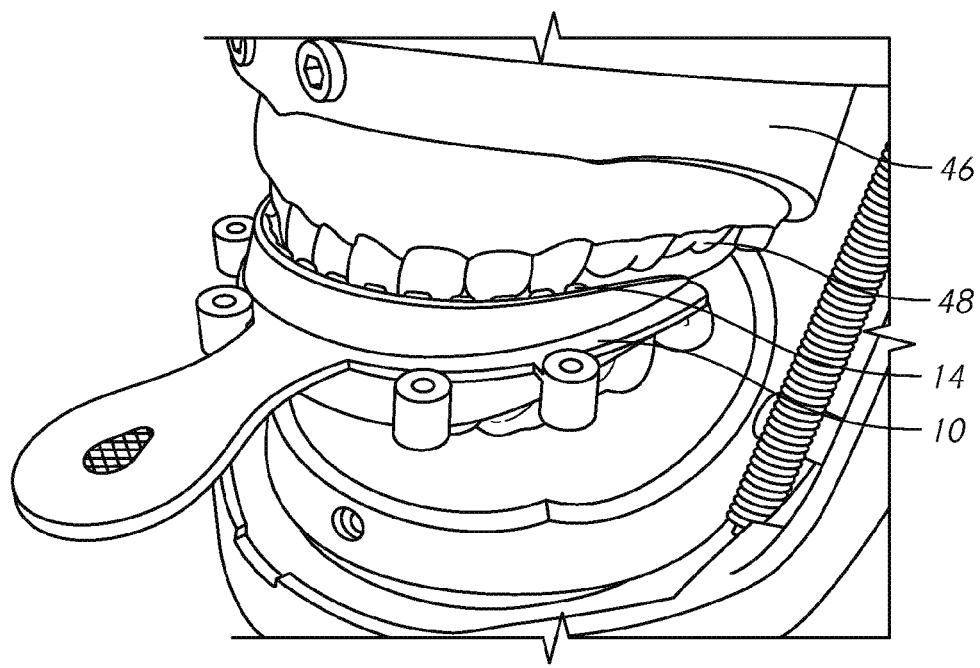
FIG. 5 is perspective view of a patient biting a bite tray making impressions of his teeth in the settable compound.

FIG. 5 is perspective view of a patient 36 biting the bite tray 10 to make impressions of his teeth 38 in the settable compound 14.

Figure 6:
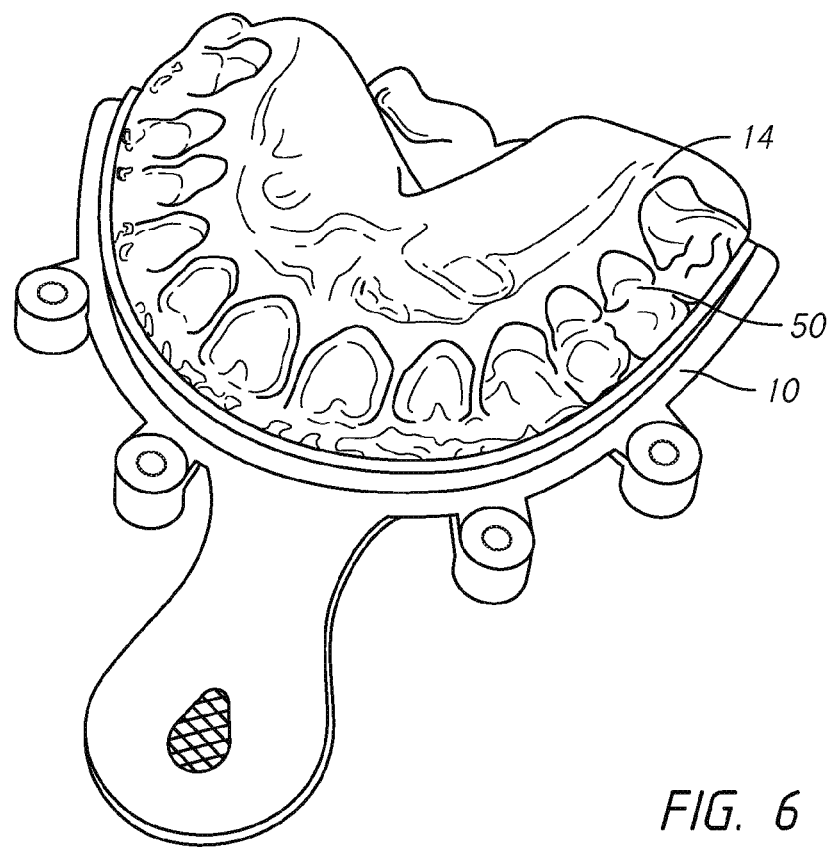
FIG. 6 shows the impressions of the teeth.

FIG. 6 shows the impressions 40 of the teeth in the settable compound 14. The settable compound 14 is then allowed to harden. The bite tray 10 is then reinserted between the teeth of the patient prior to making the x-ray, CT, or MRI scan. The bite tray may also be reinserted between the teeth after a procedure is completed which places the fiducial markers in the same position as before. A new scan can then be made that can be compared to the original scan for checking the results of the procedure.

Figure 7:
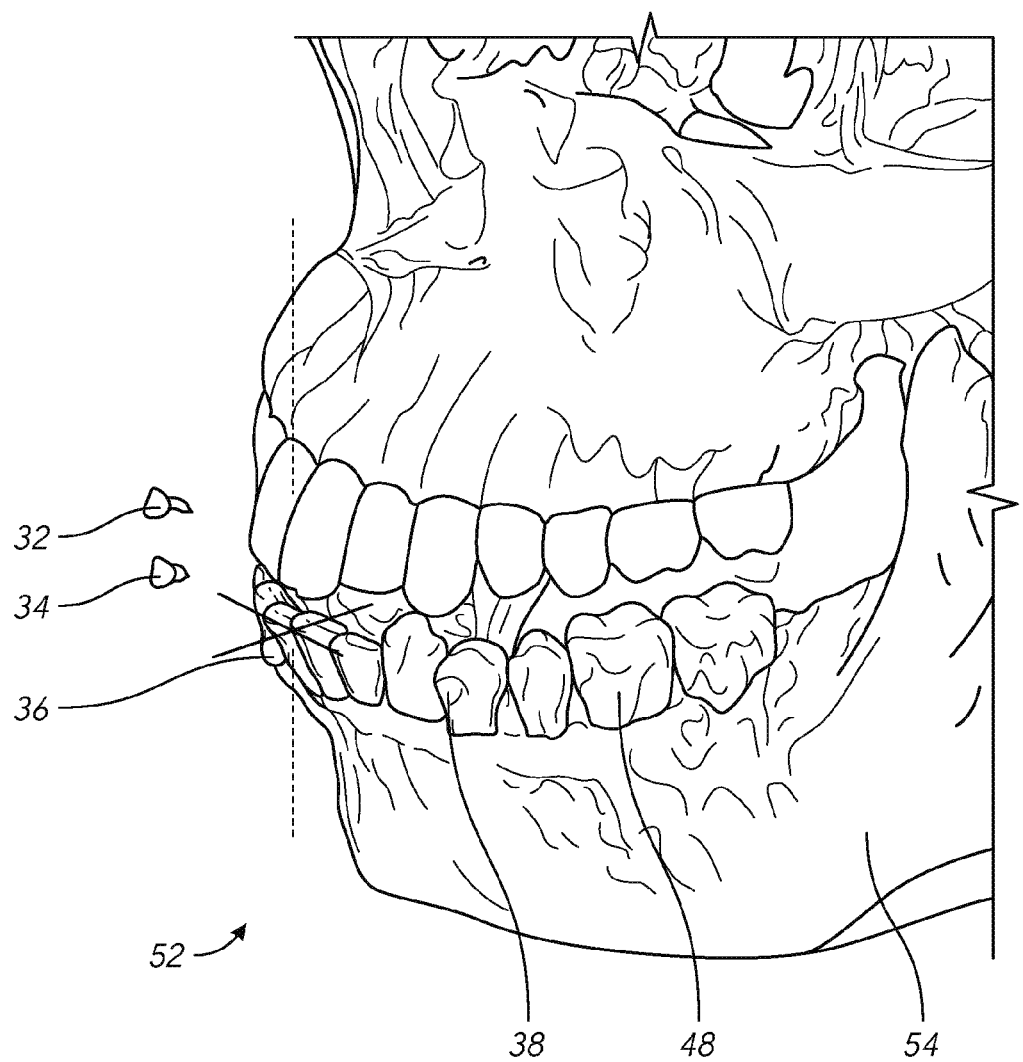
FIG. 7 is a CT or MM scan image of the head with the bite tray in place showing the fiducial markers.

FIG. 7 is an x-ray, CT or MRI scan image 52 of the head with the bite tray in place between the teeth 48 of the patient showing the fiducial markers 32, 34, 36 and 38. The bite tray does not show because its density is much less than the density of the bones 54 and teeth 48 of the patient. The fiducial markers do show because they are made of ceramic material that has substantially the same density as the bones and teeth of the patient. The fiducial markers are further marked on the scan image for better identification.

Figure 8:
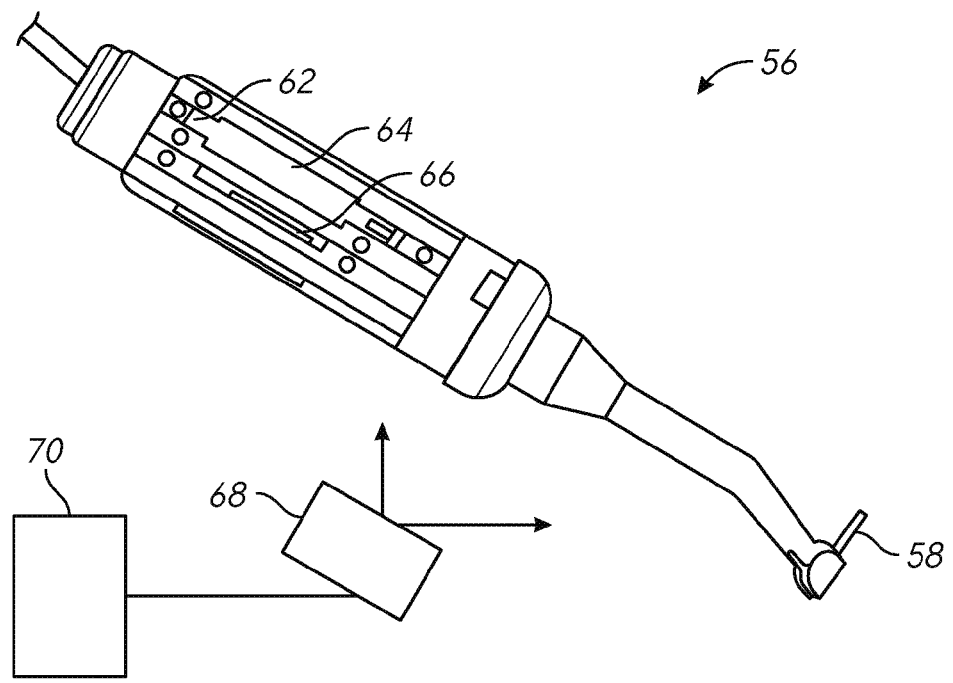
FIG. 8 shows an instrument having an operating tip and instrument markers being observed by a spatial tracking device that delivers the data to a data processing device.

FIG. 8 shows a typical dental instrument 56 having an operating tip 58 and instrument optical markers 62, 64, and 66. A spatial tracking device 68 such as an optical or infrared camera is used for observing the instrument including the operating tip and the instrument optical markers and the overall profile of the instrument. The results of the optical or infrared observation are sent to a data processing device 70 such as a computer.

Figure 9:
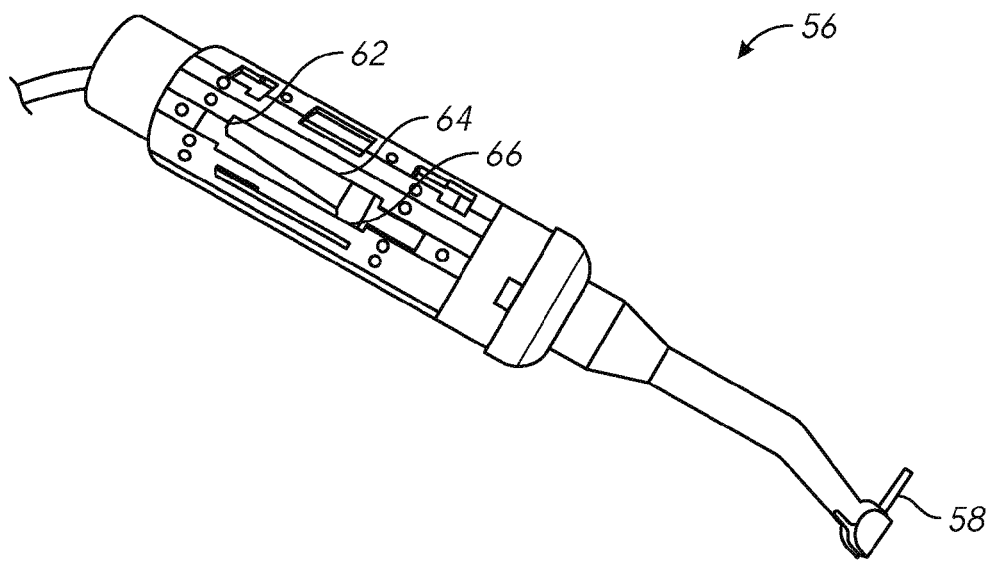
FIG. 9 shows an image of the instrument after it is analyzed by the data processing device.

FIG. 9 shows an image of the instrument 56 created by the data processing device after the instrument is analyzed including the registration of the operating tip 58 to the instrument optical markers 62, 64, and 66. The image is then available to be superimposed on the scan of the head.

Figure 10:
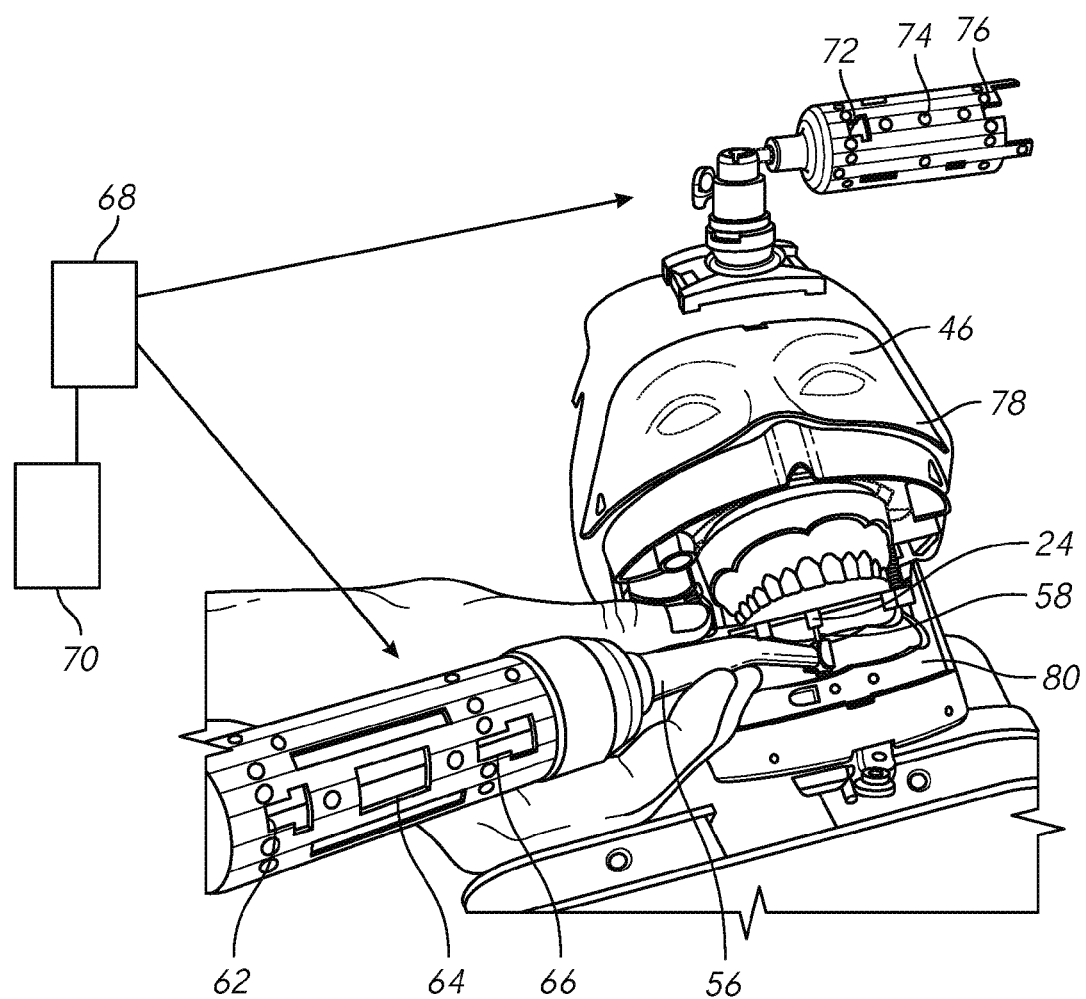
FIG. 10 shows patient markers attached to the head of a patient and the operating tip of the instrument touching a fiducial marker, the spatial tracker observing the instrument optical markers and patient optical markers, and the data transmitted to the data processing device.

FIG. 10 shows patient markers 72, 74, and 76 attached to the top of the head 78 of the patient 46 away from the jaw 80. The patient markers are the reference for the location of the patient in subsequent steps. The operating tip 58 of the instrument 56 is touching the fiducial marker 34 inside a fiducial marker holder 24. The spatial tracking device 68 observes the instrument optical markers 62, 64, and 66 and the patient optical markers 72, 74, 76 at this location and transmits the data to the data processing device 70. At that moment, the relationship of the fiducial marker 34 and the operating tip 58 of the instrument 56 are identical. The data processing device can then compute the registration of the instrument 56 and patient 46 to each other and to the scan image 52. The operating tip of the instrument can also be touched to the other fiducial markers on the bite tray. The spatial tracking device then observes the operating tip, the instrument optical markers, and the patient optical markers at the other locations and transmits the data to the data processing device 70.

Figure 11:
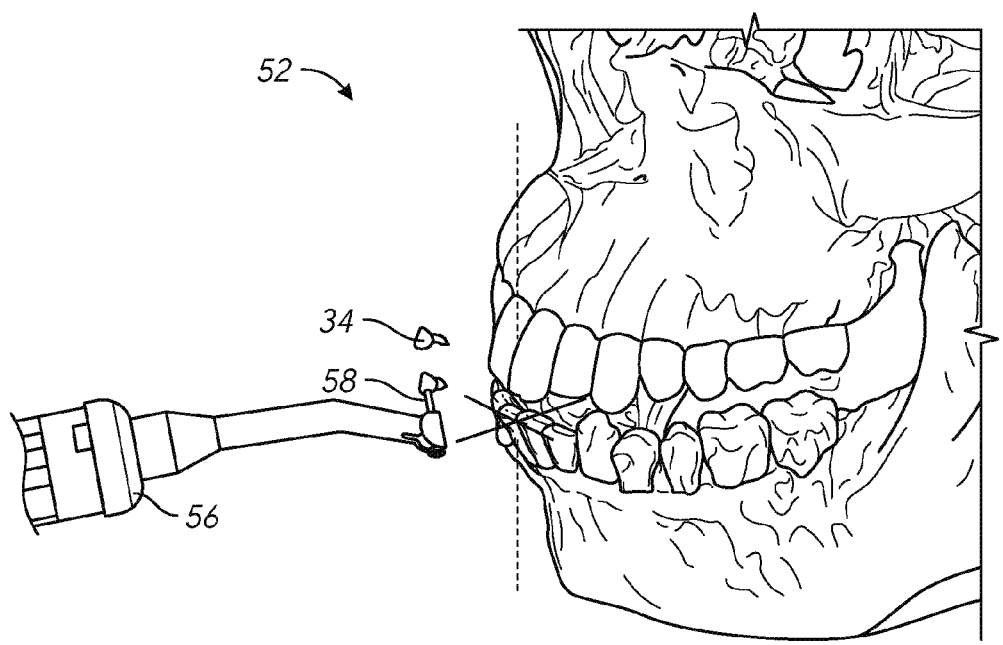
FIG. 11 shows the image of the instrument on the scan image of the head when the operating tip is touching a fiducial marker.

FIG. 11 is a scan image 52 of the head with the operating tip 58 of the instrument 56 superimposed on the scan image when the operating tip touches the fiducial marker 34 in the bite tray.

Figure 12:
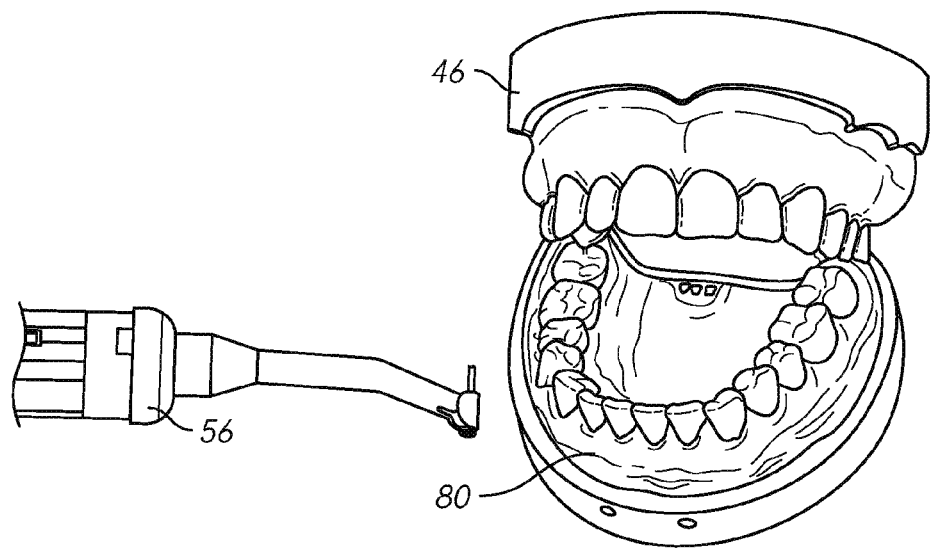
FIG. 12 shows the instrument moved off of the bite tray and the bite tray removed from the patient.

FIG. 12 shows the instrument 56 moved off of the bite tray and the bite tray removed from the jaw 80 of the patient 46.

Figure 13:
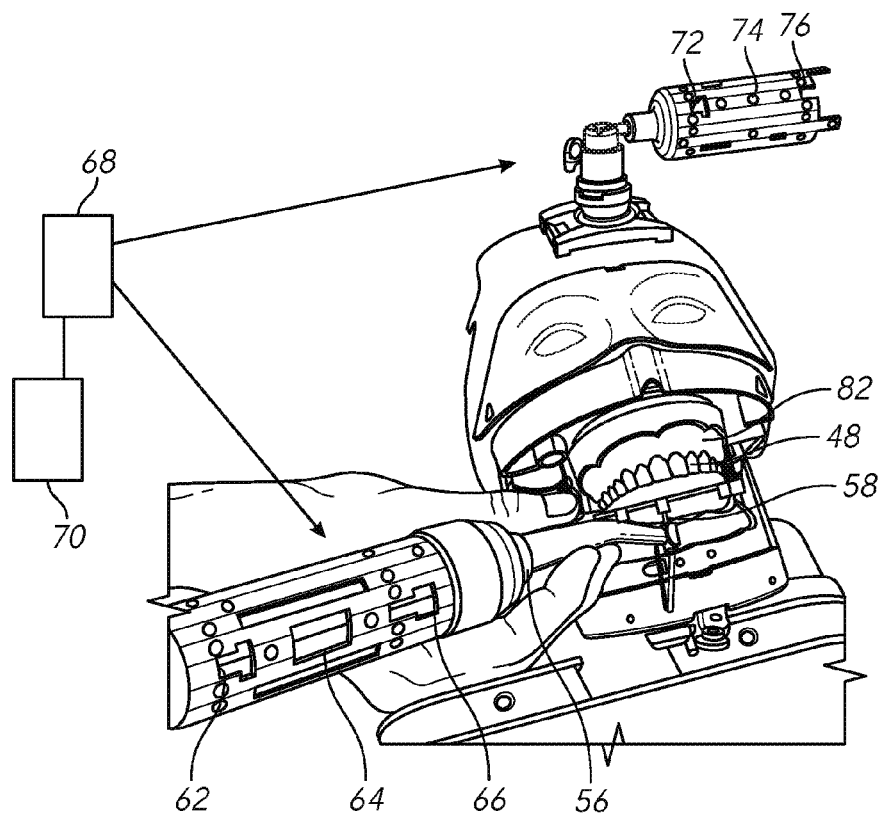
FIG. 13 shows the bite tray removed and the spatial tracking device observing the instrument optical markers and patient optical markers after the operating tip is moved back to the upper jaw and the data delivered to the data processing device.

FIG. 13 shows the operating tip 58 of the dental instrument 56 moved to the upper jaw 82 after the bite tray has been removed. The spatial tracking device 68 observes the instrument optical markers 62, 64, and 66 and the patient optical markers 72, 74, and 76 and delivers the data to the data processing device 70.

Figure 14:
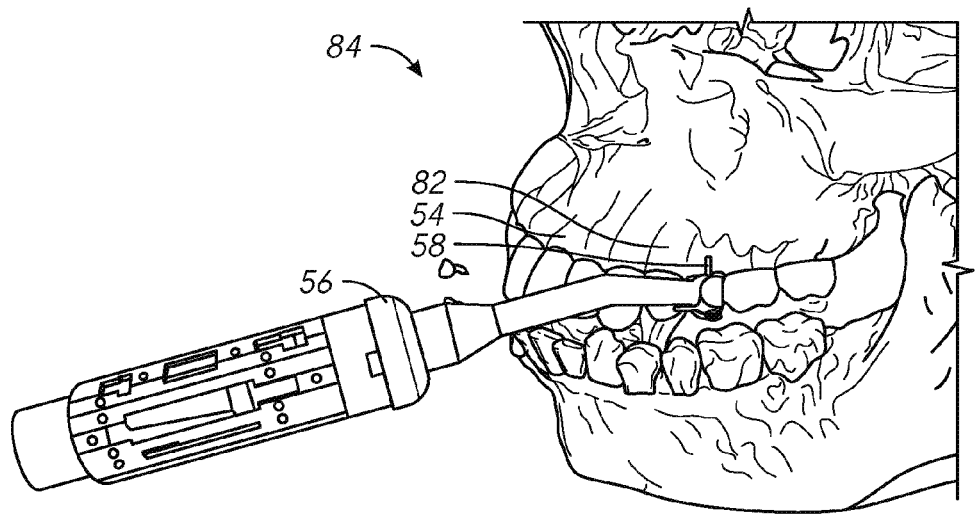
FIG. 14 shows the instrument superimposed on the scan image of the jaw.

FIG. 14 shows the operating image 86 compiled by the data processing device of the arrangement shown in FIG. 13. The instrument 56 and operating tip 58 are superimposed on the previously stored scan image 52. The operating tip 58 is adjacent the upper jaw 82. As the oral surgeon moves the operating tip 58, the process is tracked in real time by the spatial tracking device observing the instrument optical markers (FIG. 13) and the results are posted on the operating image 86 enabling the oral surgeon to see exactly what the operating tip 48 is doing in relation to the bone 44 of the upper jaw.

Figure 15:
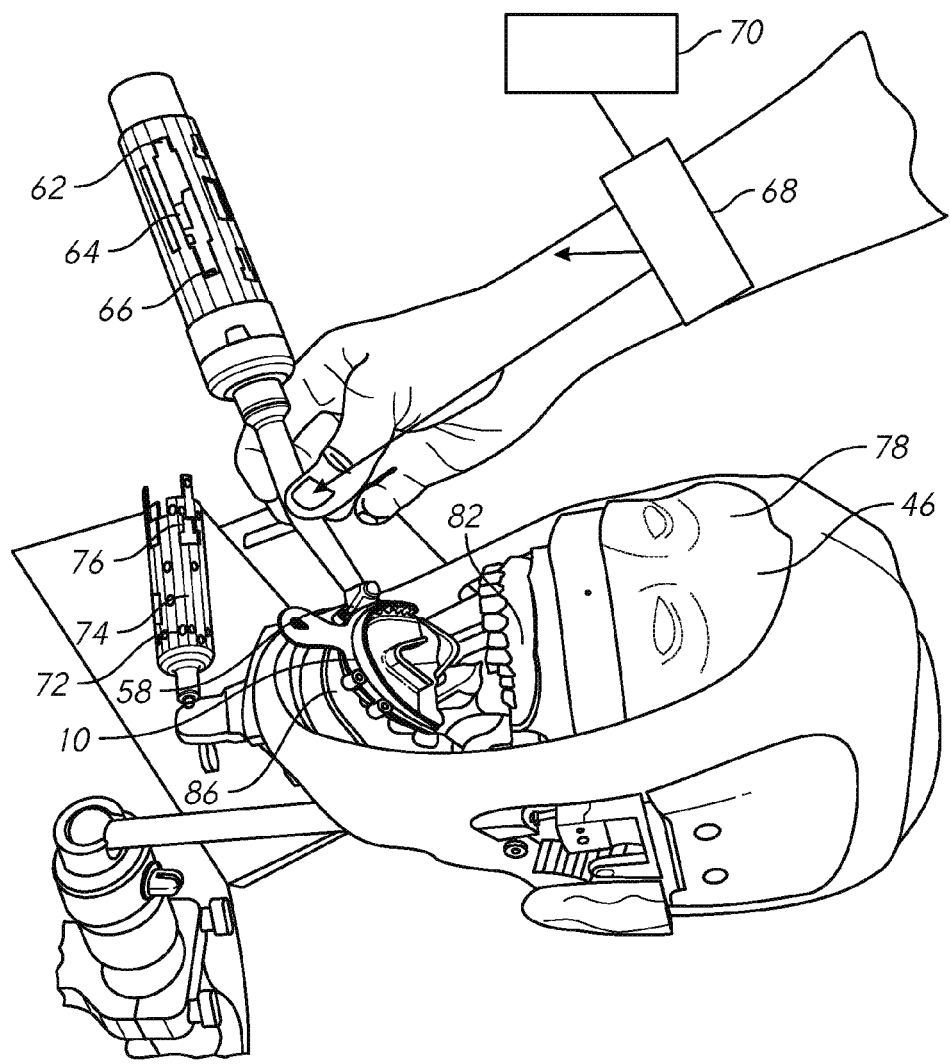
FIG. 15 shows the patient optical markers attached to the lower jaw of the patient and the operating tip of the instrument touching a fiducial marker, the spatial tracking device observing the instrument optical markers and patient optical markers, and the data transmitted to the data processing device.

FIG. 15 is similar to FIG. 13 but shows the arrangement when the oral surgeon is performing a procedure on the lower jaw 86 instead of the upper jaw 82 of the head 78. The patient optical markers 72, 74, and 76 are mounted on the lower jaw because the lower jaw is moved down for procedures on the lower jaw. Before the position shown in FIG. 15, the patient 46 has compressed the bite tray 10 in the manner shown in FIG. 5 and then lowered his jaw to the position shown in FIG. 15 with the bite tray remaining on the lower teeth. A scan image is then made with the lower jaw and bite tray in this position creating a scan image like the scan image shown in FIG. 7 but with the lower jaw lowered. The spatial tracking device 68 observes the instrument optical markers 62, 64, and 66 and patient optical markers 72, 74, and 76 in this position and delivers the data to the data processing device 70. The data processing device compiles an operating image like operating image 84 shown in FIG. 14 but with the lower jaw lowered. The operating tip 58 is touched to one or more of the fiducial markers in the bit tray 10 to register the instrument and patient to the scan image in the same manner as discussed above with respect to procedures on the upper jaw.

Figure 16:
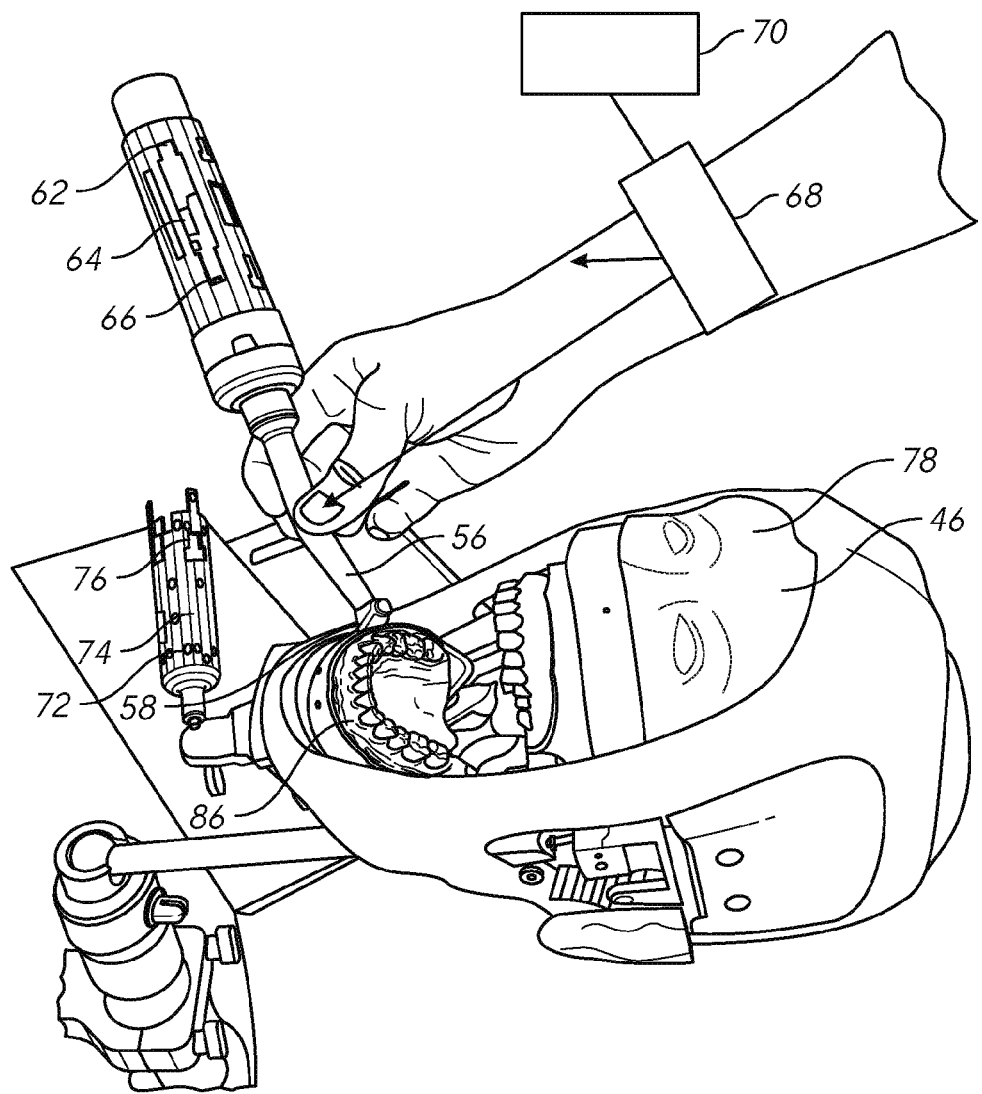
FIG. 16 shows the bite tray removed and the spatial tracking device observing the instrument optical markers and patient optical markers after the operating tip is moved back to the lower jaw and the data delivered to the data processing device.
Figure 17:
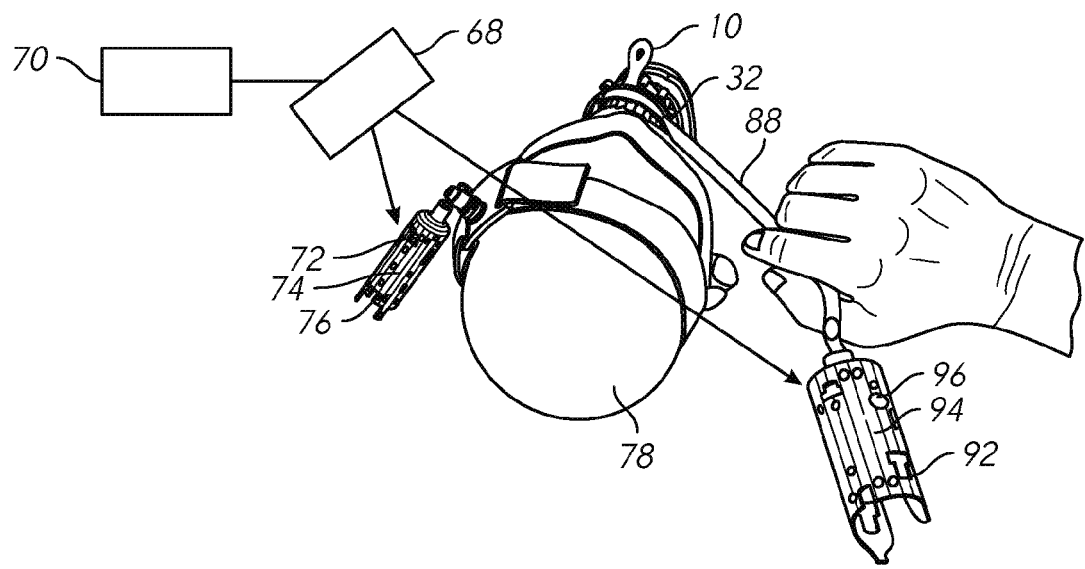
FIG. 17 shows the patient optical markers attached to the side of the head of the patient and the operating tip of the instrument touching a fiducial marker, the spatial tracking device observing the instrument optical markers and patient optical markers, and the data transmitted to the data processing device.

FIG. 16 shows the operating tip 58 of the dental instrument 56 moved to the lower jaw 86 after the bite tray has been removed. The spatial tracking device 68 observes the instrument optical markers 62, 64, and 66 and the patient optical markers 72, 74, and 76 and delivers the data to the data processing device 70. The data processing device creates an operating image similar to the operating image 84 shown in FIG. 14 but on the lower jaw. The operating surgeon can then monitor his procedure on the lower jaw in real time as it progresses FIG. 17 shows the patient optical markers 72, 74, and 76 attached to the side of the head 78 for performing a procedure on the head. A scan image 52 of the head 78 has previously been made as describe in conjunction with FIGS. 3-7. With spatial tracking device 68 observing the procedure as described above, a medical instrument 88 such as a craniotome having medical instrument optical markers 92, 94, and 96 touches fiducial marker 32 in the bite tray 10. The spatial tracking device observes the moment of touching and location of the patient optical markers 72, 74, and 76 and instrument optical markers 92, 94, and 96 and sends the data to the data processing device 70.

Figure 18:
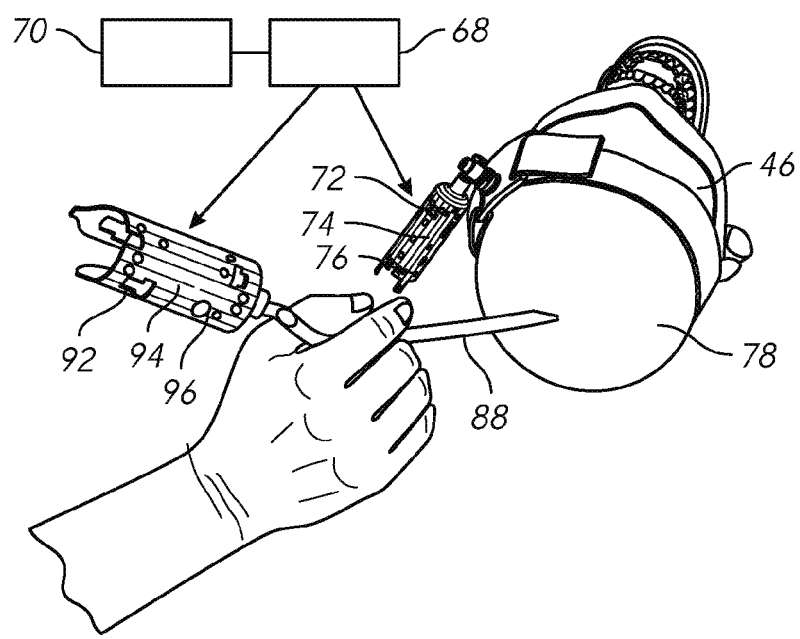
FIG. 18 shows the bite tray removed and the spatial tracking device observing the instrument optical markers and patient optical markers after the operating tip is moved to the top of the head for performing a procedure on the head and the data delivered to the data processing device; and, FIG. 19 shows magnetic instrument markers mounted near the operating end of an instrument and magnetic sensors mounted on a patient.

FIG. 18 shows the bite tray removed. The patient can then open his jaw for insertion of instruments into the mouth or anesthesia apparatus over the nose and mouth. The medical instrument 88 is moved to the top of the head for performing a procedure on the head. A typical use would be to create a burr hole for the insertion of an external ventricular drain. Exact positioning is absolutely necessary to avoid injury to the brain. The process for guiding the instrument 88 on the head is the same as the process for guiding an instrument on the jaw. The spatial tracking device 68 observes the instrument optical markers 92, 94, and 96 and patient optical markers 72, 74, and 76 and sends the data to the data processing device. The data processing device creates an image of the medical instrument 88 superimposed on the scan image of the head in the same manner as described above in conjunction with FIG. 14. The surgeon is then able to monitor the procedure in real time on a display.

Figure 19:
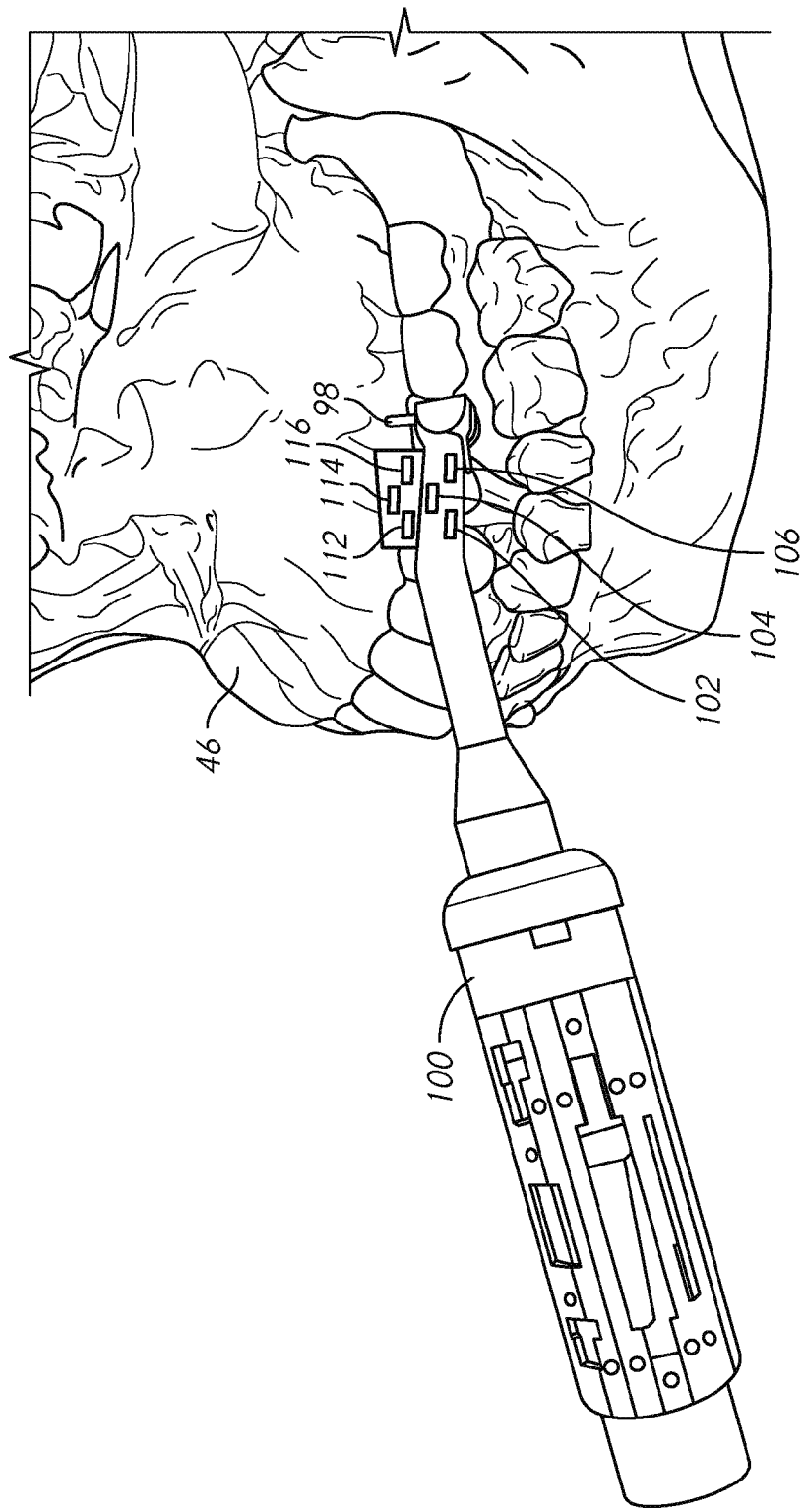

FIG. 19 shows magnetic markers being used instead of optical markers. Magnetic instrument markers 102, 104, and 106 are mounted near the operating tip 98 of a magnetic dental instrument 100 and magnetic sensors 112, 114, and 116 are mounted on a patient 46 near where the procedure is to be performed. The magnetic markers perform the same function as the optical markers of the previous embodiment. After the x-ray, CT, or MRI scan image is made with a bite tray, the magnetic sensors are attached to the patient near where the procedure is to be performed and the operating tip 98 of the instrument 100 is used to touch a fiducial marker on the bite tray as described above in conjunction with FIGS. 13 and 14 to register the scan image, instrument, and patient to each other. The bite tray is then removed and the procedure continues with the relationship of the magnet instrument markers 102, 104, and 106 and the magnetic sensors 112, 114, and 116 to each other providing data to the data processing device. The data processing device in turn creates the image of the instrument 100 superimposed on the scan image as describe and shown in FIG. 14.

The embodiments of the bite tray as a registration device and method of use described herein are exemplary and numerous modifications, combinations, variations, and rearrangements can be readily envisioned to achieve an equivalent result, all of which are intended to be embraced within the scope of the appended claims. Further, nothing in the above provided discussions of the registration device and method should be construed as limiting the invention to a particular embodiment or combination of embodiments. The scope of the invention is defined by the appended claims.

We claim:

1. A method for displaying the tip of an instrument superimposed on an image created by a scan of the head of a patient, comprising:
   providing a bite tray having a floor positionable between the teeth of a patient when clamped together, an inside teeth perimeter ridge coupled to the floor for fitting inside of the teeth of the patient, an outside teeth perimeter ridge coupled to the floor for fitting outside of the teeth of the patient, and at least three fiducial markers positioned outside of the outside perimeter ridge;

providing a settable compound in the bite tray between the inside and outside teeth perimeter ridges;

inserting the bite tray between the teeth of the patient;

having the patient clamp the bite tray between the teeth making impressions of the teeth in the settable compound;

removing the bite tray from between the teeth;

allowing the settable compound to set making the impressions of the teeth permanent;

inserting the bite tray with the permanent impressions of the teeth between the teeth of the patient;

having the patient bite the bite tray between the teeth into the permanent impressions;

providing a scanner, a data processing device, and a display;

scanning the head of the patient, the bite tray, and the at least three fiducial markers with the scanner and inputting the data to the data processing device;

having the data processing device use the data from the scanner to create an image on the display of the head of the patient with the at least three fiducial markers;

observing the image and marking the positions of the at least three fiducial markers on the image;

providing a spatial tracker for inputting data into the data processing device;

providing an instrument having an operating tip and at least three instrument optical markers;

using the spatial tracker to observe the operating tip and the at least three instrument optical markers and inputting the data to the data processing device;

having the data processing device register the relationship between the operating tip and the at least three instrument optical markers and create an image of the instrument on the display;

providing at least three patient optical markers;

attaching the at least three patient optical markers to the head of the patient away from the patient's teeth;

touching the operating tip of the instrument to at least one of the at least three fiducial markers on the bite tray;

using the spatial tracking device to observe the at least one touch of the operating tip to at least one fiducial marker and simultaneously at the at least three instrument optical markers and the at least three patient optical markers, and inputting the data to the data processing device;

having the data processing device use the data of the at least one touch to register the relationship of the scan to the instrument markers and the patient markers, displaying the image of the operating tip and instrument on the image of the patient's head on the display;

removing the bite tray from the patient;

moving the instrument;

using the spatial tracking device to observe the at least three instrument optical markers and the at least three patient optical markers and inputting the data to the data processing device; and, having the data processing device compute the relationships between the current position of the operating tip based on the current positions of the at least three instrument optical markers and the at least three patient optical markers and displaying the image of the operating tip and instrument on the scan image of the patient's head on the display.

2. The method for displaying the tip of an instrument according to claim 1, further comprising:

touching the operating tip of the instrument to at least three of the at least three fiducial markers on the bite tray;

using the spatial tracking device to observe the at least three touches of the operating tip to the at least three fiducial marker and simultaneously at the at least three instrument optical markers and the at least three patient optical markers, and inputting the data to the data processing device;

having the data processing device use the data of the at least three touches to register the relationship of the scan to the instrument markers and the patient markers; and, displaying the image of the operating tip and instrument on the image of the patient's head on the display.

3. The method for displaying the tip of an instrument according to claim 1, further comprising:

the step of attaching the at least three patient optical markers to the head of the patient away from the patient's teeth further includes attaching the at least three patient optical markers on the top of the head of the patient;

after the step of removing the bite tray from the patient, having the patient lower his lower jaw from his upper jaw;

moving the operating tip of the instrument against the patient's upper jaw;

monitoring the position of the operating tip on the image of the operating tip on the image of the head on the display; and, adjusting the operating tip of the instrument against the upper jaw based on the information provided by the scan image of the head and image of the operating tip on the display.

4. The method for displaying the tip of an instrument according to claim 1, further comprising:

the step of attaching the at least three patient optical markers to the head of the patient away from the patient's teeth further includes attaching the at least three patient optical markers on the lower jaw of the patient;

after the step of removing the bite tray from the patient, having the patient lower his lower jaw from his upper jaw;

moving the operating tip of the instrument against the patient's lower jaw;

monitoring the position of the operating tip on the image of the operating tip on the scan image of the head on the display; and, adjusting the operating tip of the instrument against the lower jaw based on the information provided by the scan image of the head and image of the operating tip on the display.

5. The method for displaying the tip of an instrument according to claim 1, further comprising:

the step of attaching the at least three patient optical markers to the head of the patient away from the patient's teeth further includes attaching the at least three patient optical markers on the side of the head of the patient;

after the step of removing the bite tray from the patient, moving the operating tip of the instrument against the head;

monitoring the position of the operating tip on the image of the operating tip on the scan image of the head on the display; and, adjusting the operating tip of the instrument against the head based on the information provided by the scan image of the head and image of the operating tip on the display.

* * * * *